United States Patent [19]
Corwin et al.

[11] Patent Number: 6,136,785
[45] Date of Patent: Oct. 24, 2000

[54] PROTECTION FROM LOSS OF SENSORY HAIR CELLS IN THE INNER EAR BY ADMINISTRATION OF INSULIN-LIKE GROWTH FACTOR AND PLATELET DERIVED GROWTH FACTOR

[75] Inventors: Jeffrey T. Corwin; Eugenia Gray; Mark E. Warchol; Linda D. Saffer, all of Charlottesville, Va.

[73] Assignee: University of Virginia Patent Foundation, Charlottesville, Va.

[21] Appl. No.: 09/376,370

[22] Filed: Aug. 18, 1999

Related U.S. Application Data

[63] Continuation of application No. 08/693,410, Aug. 7, 1996.
[60] Provisional application No. 60/002,033, Aug. 8, 1995.

[51] Int. Cl.[7] ................................................ A61K 38/00
[52] U.S. Cl. .............................. 514/12; 514/3; 530/399; 435/6; 435/7.8
[58] Field of Search ...................... 514/3, 12; 530/399; 435/6, 7.8

*Primary Examiner*—Dwayne C. Jones
*Assistant Examiner*—C. Delacroix-Muirheid
*Attorney, Agent, or Firm*—Oblon, Spivak, McClelland, Maier & Neustadt, P.C.

[57] ABSTRACT

The invention relates to a method for protecting sensory hair cells of the inner ear from damage caused by ototoxic drugs, in particular, aminoglycoside antibiotics, by administering to a vertebrate a growth factor, or mixture thereof. Additionally, the method protects against loss of sensory hair cells as a result of aging. In particular, the growth factor is an insulin-like growth factor or platelet-derived growth factor. The invention also relates to a method for detecting protection against an ototoxic drug on sensory hair cells of an inner ear of a vertebrate by a growth factor or biologically active fragment.

8 Claims, 10 Drawing Sheets

PROTECTION FROM LOSS OF SENSORY HAIR CELLS IN THE INNER EAR BY ADMINISTRATION OF INSULIN-LIKE GROWTH FACTOR AND PLATELET DERIVED GROWTH FACTOR

CROSS-REFERENCE TO RELATED APPLICATIONS

This application is a continuation of Ser. No. 08/693,410, filed Aug. 7, 1996, which claims priority from U.S. Provisional Application Ser. No. 60/002,033, filed Aug. 8, 1995, which is incorporated by reference herein in its entirety.

GOVERNMENT SUPPORT

This invention was made with government support under grants R01-DC00200 and R29-DC02291 awarded by the National Institute of Health. The government may have certain rights in the invention.

BACKGROUND OF THE INVENTION

1. Field of the Invention

The present invention relates to a method for protecting sensory hair cells of the inner ear by administering a growth factor. In particular, the method of present invention protects sensory hair cells from apoptotic death caused by ototoxic drugs such as aminoglycoside antibiotics. In a preferred embodiment, Insulin-Like Growth Factor-1 (IGF-1) and Platelet-Derived Growth Factor (PDGF) are used to prevent the apoptotic death of hair cells.

2. Discussion of the Background

The sensory hair cells of the inner ear play an essential role in hearing and balance. Hair cells are the mechanoreceptive transducers for sound and balance in the inner ear. Hair cell loss caused by loud sound, drug treatments, infections, or aging results in permanent hearing and balance deficits that affect millions of people. In fish and amphibians these cells are produced throughout life and damaged cells can be replaced. (Corwin, J. T. (1981) *J. Comp. Neurol.* 201: 541–553; Corwin, J. T. (1983) *J. Comp. Neurol.* 217:345–356; Corwin, J. T. (1985) *Proc. Natl. Acad. Sci. USA* 82:3911–3915; Lombarte, A., et al. (1993) *Hear. Res.* 64:166–174; Baird, R. A. and Torres, M. A. (1993) *Hear. Res.* 65:164–174.) In birds and mammals, all auditory hair cells normally are produced before birth (Ruben, R. J. (1967) *Acta Otolarnygol. Suppl.* 220:1–44; Katayama A. and Corwin, J. T. (1989) *J. Comp. Neurol.* 281:129–135.) Birds can, however, regenerate their hair cells. Loss of hair cells is followed by self-repair stemming from trauma-evoked mitosis in supporting cells and the differentiation of replacement hair cells at sites of lesions (Cotanche, D. A. (1987) *Hear. Res.* 30:181–196; Corwin, J. T. and Cotanche, D. A. (1988) *Science* 240:1772–1774; Ryals, B. M. and Rubel, E. W. (1988) *Science* 240:1774–1776.) In fact, the supporting cells of a wide range of auditory, vestibular, and lateral line epithelia of non-mammalian vertebrates can divide to give rise to new cells which can either continue to proliferate, or differentiate as supporting cells or hair cells (Corwin, J. T. (1986) Regeneration and self-repair in hair cell epithelia experimental evaluation of capacities and limitations. In: R. J. Ruben, T. R. Van DeWater and E. W. Rubel (Eds.) *Biology of Change in Otolaryngology,* Elsevier, N.Y., pp. 291–304.; Cotanche, D. A. (1987) *Hear. Res.* 30:181–196.; Corwin, J. T. and Cotanche, D. A. (1988); Jorgenson, J. M. and Mathiesen, C. (1988) *Naturwissenschaften* 7:319–320.; Girod, D. A., et al (1989) *Assoc. Res. Otolaryngol. Abstr.* 12:84–85; Balak, K. J., et al (1990) *J. Neurosci.* 10:2502–2512; Jones, J. E. and Corwin, J. T. (1993) *J. Neurosci.* 13:1022–1034.; Raphael, Y. (1992) *J. Neurocytol,* 21:663–671; Raphael, Y. (1993) *J. Comp. Neurol.* 330:521–532, Weisleder, P. and Rubel, E. W. (1993) *J. Comp. Neurol.* 331:97–110.)

Loss of hair cells from the cochlea and balance organs (cochleotoxicity and vestibulotoxicity) is among the unfortunate side effects of the aminoglycosides, a class of antibiotics based on a structure of glycosidically linked aminocyclitol rings. The primary mode of aminoglycoside ototoxicity is not known, although the toxicity may result from the interaction of the drugs with inner ear phosphoinositides (S. L. Garetz and J. Schacht, in *Clinical Aspects of Hearing* T. N. Van De Water, A. N. Popper, and R. R. Fay, eds., Springer, 1996. pp. 116–153.)

Apoptosis is a physiologically active form of cell death that is characterized by cellular fragmentation, formation of pyknotic nuclei, and fragmentation of DNA into 180–200 basepair units. Apoptotic cells can be recognized either by histologic examination of nuclei, or by staining of digoxigenin-tagged DNA fragments. Cochlear and vestibular hair cells have been shown to undergo apoptosis in response to application of aminoglycoside antibiotics (J. Kil, et al, Association for Research in otolaryngology, 18th Midwinter Research Meeting, St. Petersburg Beach, Fla. Abstract 328), and exposure to high-intensity noise (J. C. Mason, et al, Society for Neuroscience, 25th Annual Meeting, San Diego Calif., Abstract 164.5).

Supporting cells often survive trauma that kills neighboring hair cells. This is true in all vertebrates, including mammals, so the surviving supporting cells may be a source of new epithelial cells that could be manipulated to enhance regenerative responses. The vestibular organs in mammals share structural characteristics with the sensory epithelia of the ears of non-mammalian species that produce hair cells during postembryonic life, suggesting that the mammalian vestibular epithelia might have a capacity for regeneration of hair cells (Corwin, J. T. (1986) Regeneration and self-repair in hair cell epithelia experimental evaluation of capacities and limitations. In: R. J. Ruben, T. R. Van DeWater and E. W. Rubel (Eds.) *Biology of Change in Otolaryngology,* Elsevier, N.Y., pp. 291–304.) Recently, morphological studies demonstrated the reappearance of immature-appearing hair bundles and hair cell bodies at sites of lesions in the utricles of guinea pigs that were fixed 4 weeks after the end of a 10-day treatment with gentamicin (Forbe et al, (1993) *Science* 259:1616–1619.) Proliferation of supporting cells was demonstrated in a parallel study after hair cell loss caused by gentamicin and neomycin treatments of utricles from juvenile and adult guinea pigs and adult humans in vitro (Warchol et al., (1993) *Science* 259:1619–1622.) Labeled putative replacement hair cells were observed in utricles that had been cultured for 4 weeks after the aminoglycoside treatment.

In order for non-cancerous cells to proliferate, they require the binding of mitogenic growth factors to specific receptors on their cell surfaces. Binding and the subsequent dimerization that occurs for many types of tyrosine kinase receptors activates signaling cascades within the cell to take the cell from a resting state, $G_0$, back to $G_1$, and into S-phase, where DNA is replicated (Pardee (1989) *Science* 246:603–608.) Growth factors can also participate in the regulation of cell differentiation and are required as positive signals for cell survival (McKay and Leigh (1993) *Growth Factors: A Practical Approach.* Oxford University Press, New York, N.Y.; Raff et al (1993) *Science* 262:695–700.)

The nature of a tissue's responsiveness to growth factors is regulated by the availability of growth factor ligands and the expression of specific growth factor receptor types on the surfaces of the cells. The sequences for many messenger RNAs have been determined for rats, and a number of sequences for growth receptors have been published.

A number of growth factors and cytokines have been shown to rescue neural cell types from apoptotic death. For example, the factor IGF-1 has been reported to promote the survival of spinal motor neurons in several types of experimental neuropathologies [J. L. Vaught, P. C. Contreras, M. A. Glicksman, and N. T. Neff in *Growth Factors as Drugs for Neurological and Sensory Disorders* (Ciba Foundation Symposium 196) Wiley, 1996. pp. 18–27]. [The structure of IGF-1 and the IGF family of molecules is described in: M. M. Rechler and S. P. Nissley: Insulin-Like Growth Factors in: *Peptide Growth Factors and their Receptors*, M. B. Sporn and A. B. Roberts, eds. Springer 1990. pp. 263–367]

In view of the aforementioned side-effects to the sensory hair cells of the inner ear attendant with the administration of ototoxic drugs, it is clear that there exists a need in the art for a method of preventing or treating such side-effects.

SUMMARY OF THE INVENTION

Accordingly, one object of this invention is to provide a novel method for protecting sensory hair cells of the inner ear from damage caused by ototoxic drugs, by administering a growth factor.

With the foregoing and other objects, advantages and features of the invention that will become hereinafter apparent, the nature of the invention may be more clearly understood by reference to the following detailed description of the preferred embodiments of the invention and to the appended claims.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 6 shows cross-sections of rat utricles.

FIG. 9 shows fluorescent antibody staining of rat utricles.

DESCRIPTION OF THE PREFERRED EMBODIMENTS

Figure 1A:
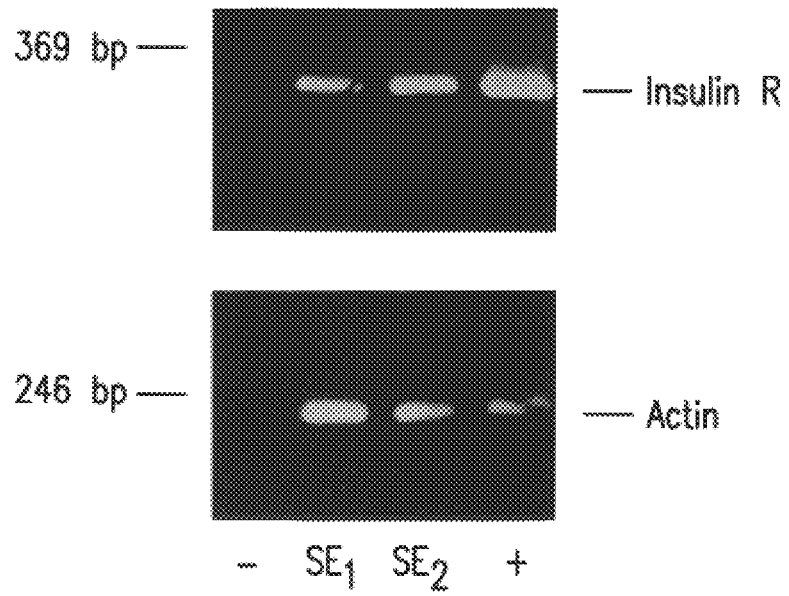
FIG. 1(A and B) shows amplified fragments for Insulin R mRNA and β-actin mRNA from control (A) and neomycin-damaged (B) sensory epithelia of rat utricles. The mRNA was reverse transcribed to cDNA before amplifying. Fragments of predicted size, 300 bp for Insulin R and 243 bp for actin, were visualized in a 3% metaphor gel wiLth Sybr Green I dye. Numbers refer to base pairs of DNA standards: SE, sensory epithelium; −, negative control, amplification of sequences in DEPC water; +, positive control, amplification of sequences in rat brain.

The present invention demonstrates that growth factors inhibit aminoglycoside-induced apoptosis of sensory hair cells in the saccule, a vestibular sensory organ that detects linear acceleration. Receptors for the growth factors, in particular insulin receptor (Insulin R), insulin-like growth factor I receptor (IGF-IR), fibroblast growth factor receptor (FGFR-1), epidermal growth factor receptor (EGFR) and platelet-derived growth factor α receptor (PDGF-αR) are present on the hair cells of the vestibular epithelia. Thus, these growth factors have application as a means of preventing and treating peripheral hearing and balance disorders.

As used herein, the phrase "pharmaceutically acceptable" refers to molecular entities and compositions that are physiologically tolerable and do not typically produce an allergic or similar untoward reaction, such as gastric upset, dizziness and the like, when administered to a human.

The phrase "therapeutically effective amount" as used herein to mean an amount sufficient to prevent, and preferably reduce by at least about 10 percent, more preferably by at least 25 percent, most preferably by at least 35 percent, of sensory hair cell loss in the presence of an ototoxic drug, or due to aging.

The method of the present invention may be performed on any vertebrate, but preferably on mammals, including humans. Any growth factor which can protect sensory hair cells of the inner ear from damage by ototoxic drugs. Such growth factors may include epidermal growth factor (EGF), fibroblast growth factor (acidic or aFGF or basic, bFGF, FGF-3, 4, 5, 6, 7, etc), insulin-like growth factors (IGF-1, IGF-2, etc.), nerve growth factor (NGF), platelet-derived growth factor (PDGF; AA, AB and BB forms), the interleukins, transforming growth factor (TGF-α, TGF-β) and the like. Preferably, the growth factors include the IGFs and PDGF.

The compounds have preventative actions when delivered by topical application, when delivered by implanted or external pump, when delivered by intravenous, intradermal, subcutaneous, intramuscular, intrathecal, intraperitoneal, or intraortic injection, when delivered orally, rectally, via ear drops, via release from an implanted slow-release polymer or resin, or when delivered via injection or implantation of genetically engineered cells lines, or when delivered by release of IGF's from binding proteins.

The present invention naturally contemplates several means for preparation of the growth factor to be administered, including known recombinant techniques, and the invention is accordingly intended to cover such synthetic preparations within its scope. The knowledge of the cDNA and amino acid sequences of these growth factors facilitates the reproduction of the growth factors by such recombinant techniques, and accordingly, the invention also contemplates the use of expression vectors for the delivery of the growth factor by both ex vivo and in vivo techniques.

As discussed earlier, the growth factors may be prepared in pharmaceutical compositions, with a suitable carrier and at a strength effective for administration by various means to a vertebrate which is exposed to an ototoxic agent, or is exhibiting an adverse medical condition associated with a loss of hearing or impaired vestibular function for the treatment thereof. A variety of administrative techniques may be utilized, among them parenteral techniques such as subcutaneous, intravenous and intraperitoneal injections, catheterizations and the like. Average quantities of the growth factor may vary and in particular should be based upon the recommendations and prescription of a qualified physician or veterinarian.

The present invention further contemplates therapeutic compositions useful in practicing the therapeutic methods of this invention. A subject therapeutic composition includes, in admixture, a pharmaceutically acceptable excipient (carrier) and one or more growth factors or biologically active fragments thereof, as described herein as an active ingredient.

The preparation of therapeutic compositions which contain growth factors, analogs or active fragments as active ingredients is well understood in the art. Typically, such compositions are prepared as injectables, either as liquid solutions or suspensions, however, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the composition can contain minor amounts of auxiliary substances such as wetting or emulsifying agents, pH buffering agents which enhance the effectiveness of the active ingredient.

A growth factor, fragments thereof, or mixtures thereof can be formulated into the therapeutic composition as neutralized pharmaceutically acceptable salt forms. Pharmaceutically acceptable salts include the acid addition salts (formed with the free amino groups of the polypeptide or antibody molecule) and which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The therapeutic growth factor-containing compositions are conventionally administered intravenously, as by injection of a unit dose, for example. The term "unit dose" when used in reference to a therapeutic composition of the present invention refers to physically discrete units suitable as unitary dosage for humans, each unit containing a predetermined quantity of active material calculated to produce the desired therapeutic effect in association with the required diluent; i.e., carrier, or vehicle.

The compositions are administered in a manner compatible with the dosage formulation, and in a therapeutically effective amount. The quantity to be administered depends on the subject to be treated and degree of inhibition or prevention of ototoxicity desired. Precise amounts of active ingredient required to be administered depend on the judgment of the practitioner and are peculiar to each individual. However, suitable dosages may range from about 0.1 to 20, preferably about 0.5 to about 10, and more preferably one to several, milligrams of active ingredient per kilogram body weight of individual per day and depend on the route of administration. Suitable regimes for initial administration and booster shots are also variable, but are typified by an initial administration followed by repeated doses at one or more hour intervals by a subsequent injection or other administration. Alternatively, continuous intravenous infusion sufficient to maintain concentrations of ten nanomolar to ten micromolar in the blood are contemplated.

The invention also includes an assay system for screening of potential growth factors effective to prevent or diminish ototoxic activity of drugs on vertebrate cells, and also for screening of drugs which potentiate the preventative effects of the growth factors. In one instance, the growth factor or test drug could be administered to a cellular sample with the ototoxic drug to determine its effect upon the ototoxicity on vertebrate cells by comparison with a control.

The assay system could more importantly be adapted to identify drugs or other entities that are capable of binding to the growth factor and/or the growth factor receptor, potentiating the protective activity.

Having generally described this invention, a further understanding can be obtained by reference to certain specific examples which are provided herein for purposes of illustration only and are not intended to be limiting unless otherwise specified.

EXAMPLES

Example 1

Since the mammalian utricle has at least some regenerative capabilities, the sensory epithelium of rat utricles was chosen for an assay for growth factor receptor messages so as to identify signals that may be required to control regeneration in those epithelia.

RT-PCR (reverse transcriptase-polymerase chain reaction) was chosen as a rapid, sensitive method to assay small numbers of cells from the utricular sensory epithelium for the expression of 5 receptor messages. Utricles were harvested from young rats and processed in three groups. For the in vivo control group, the epithelia were removed immediately after decapitation. For the in vitro damaged group and the in vitro undamaged group, the utricles were cultured for 24 h in the presence or absence of neomycin and then cultured an additional 24 h without neomycin. All undamaged sensory epithelia were found to contain mRNA for each of the growth factor receptor messages examined: Insulin R, IGF-IR, FGFR- 1, EGFR, and PDGF-αR. Neomycin-damaged sensory epithelium contained mRNA for the same receptors, but consistently appeared to have less mRNA for PDGF-αR and in many cases appeared to have less mRNA for IGF-IR.

Dissection

Utricles were removed from 36 female Sprague-Dawley rats (100–149 g) and dissected in ice-cold Hanks' balanced saline solution containing 10 mM HEPES at pH 7.4 (HHBSS). The utricles were divided into 3 groups: (1) in vivo undamaged controls, (2) in vitro neomycin-damaged, and (3) in vitro undamaged controls. The sensory epithelia for the in vivo undamaged group were harvested immediately after decapitation of control rats. Utricles were dissected from the inner ears, and the membranous roof of the utricle, the otoconia, and the otolithic membrane were removed. A thermolysin digestion method was used to separate sensory epithelia from non-sensory tissue. This was adapted from a procedure used to harvest human keratinocytes. (Germain et al (1993) *Burns* 19:99–104; Corwin et al (1995) *Assoc. Res. Otolaryngol. Abstr.* 18:87.) For this each utricle was incubated for 1.5 h at 37° C. in Medium 199 (M-199) containing Earle's salts and thermolysin (Sigma protease type X) at 500 $\mu$g/ml in a 5% $CO_2$ atmosphere. Then the enzyme solution was diluted with excess ice-cold HHBSS and kept cold as the epithelia were harvested. After the thermolysin treatment, the sensory epithelium was gently lifted from the underlying connective tissue, and the surrounding regions of non-sensory epithelia were cut away using double-edge razor blades. Isolated sheets of cells, composed of only the central part of a sensory epithelium, were harvested in this way, individually transferred to an Eppendorf tube containing 1 ml of fresh, ice-cold HHBSS, and centrifuged at 5200×g for 5 min. Then all but a few microliters of solution was removed, the tube was immersed in liquid nitrogen, and transferred to storage at −80° C.

Cultures of Utricles

Other utricles were cultured in M-199 with Earle's salts, supplemented with 5% fetal bovine serum (GIBCO), 10 U/ml penicillin (GIBCO), 0.025 mg/ml Fungizone (GIBCO), 1.2 pM cholera toxin (Sigma), either with or without 10 mM neomycin sulfate (Sigma) for 24 h at 37° C. in a 5% $CO_2$ atmosphere, depending upon whether they were in the in vitro damaged or the in vitro undamaged treatment groups. The media were removed and twice the volume of M-199 (at 37° C.) was added as a rinse and removed. Then M-199, supplemented as above but without neomycin, was added to each dish and the utricles were cultured for an additional 24 h. The sensory epithelia were treated next with thermolysin, removed from each of the cultured utricles, and handled as described above.

Extraction of RNA and RT-PCR

Total RNA was extracted from each sensory epithelium individually using Trizol (GIBCO), a phenol guanidine isothiocyanate solution (Chomczynski and Sacchi (1987) *Anal. Biochem.* 162:156–159.) Murine leukemia reverse transcriptase and random primers (Perkin-Elmer-Roche, Branchburg, N.J.) were used for reverse transcription at 42° C. for 15 min. The resulting cDNA was amplified using specific primers under optimized conditions of annealing temperatures, $MgCl_2$ concentrations, and pHs. Those conditions were determined for each PCR reaction using rat brain tissue and an Opti-Prime PCR optimization kit (Stratagene, La Jolla, Calif.). The pH was 8.3 or 8.8 and the ionic concentrations were 10 mM Tris-HCl, 1.5 mM or 3.5 mM $MgCl_2$, and 25 mM KCl. Samples were overlaid with mineral oil. The cDNA was denatured for 5 min at 95° C. before adding 2.5 U of Taq polymerase (Perkin-Elmer-Roche). Each of the 35 cycles of amplification included denaturation at 94° C. for 120 s, reannealing of primer to target sequences for 105 s at 55–65° C., depending on the sequence, and extension for 120 s at 72° C. The final extension was for 5 min.

All PCR products were electrophoresed in 3 Metaphor agarose gels (FMC, Rockland, Me.), visualized on a UV illuminator with Sybr Green I (Molecular Probes, Eugene, Oreg.), and photographed.

Oligonucleotide Primers

Insulin R, IGF-IR, EGFR, PDGF-αR, and β-actin primers were identical, or nearly identical, to previously published oligonucleotide sequences that had been used to successfully amplify fragments of these growth factor receptor messages (Watson et al (1992) *Mol. Reprod. Dev.* 31:867–95.; Pletsch et al (1990) *Mol. Cell. Biol.* 10:2973–2982.) In the case of Insulin R and β-actin a single base was changed to bring about agreement with the rat sequences. FGFR-1 primers were designed on the basis of published sequences for rat FGFR cDNA (Yazaki et al (1993) *Biochim. Biol. Acta* 1172:37–42.) The primers 5'-GAC CGT TCT GGA AGC CCT TGG AA-3' (SEQ ID NO:1) and 5'-AGA CCG ATG GCT TCG GCC AAC AC-3' (SEQ ID NO:2) were used to amplify a piece of cDNA for a region of the protein extending from the proximal part of the extracellular domain through one-third of the intracellular domain. The amplified cDNA fragments for β-actin, EGFR, and FGFR-1 contained splice sites, so any artifactual amplification of genomic DNA would have produced larger fragments than expected for the cDNA. The predicted sizes of the amplified cDNA fragments were 243 base pairs (bp) for β-actin, 300 bp for Insulin R, 359 bp for IGF-IR, 434 bp for FGFR-1, 640 bp for EGFR, and 234 bp for PDGF-αR.

RNase Precautions and Controls

RNase-free plasticware and diethyl pyrocarbonate (DEPC)—treated glassware and water were used. Three controls were included in each experimental run. Rat brain was used as a positive control and for PCR optimization, because it is known to contain mRNA for all the growth factor receptors which were assayed here. DEPC-treated water was used as a negative control to confirm that the solutions were not contaminated with cDNA. Each sample also was run in duplicate, with and without reverse transcriptase in the reaction mixture, to confirm that the amplified bands came from RNA and not from the amplification of genomic DNA or contaminating cDNA.

Semi-quantitative RT-PCR

To compare the levels of messages quantitatively it is necessary for the PCR amplification to be in the exponential phase. Aliquots of the PCR products were removed from the same tube after 10, 15, 20, 25, 30, 35, 40, and 45 cycles and bands were examined on agarose gels after staining with Sybr Green 1 to determine the curve of amplification. The intensity of each band was measured using an Eagle Eye I video system (Stratagene, La Jolla, Calif.), that was calibrated using DNA standards (GIBCO) run in the same gels and analyzed with NIH Image software.

Immunohistochemical Localization of PDGF-αR

Utricles were fixed in 4% paraformaldehyde for 30 min at room temperature. After rinsing in phosphate-buffered saline (PBS), they were incubated in 5% sucrose in PBS overnight at 4° C. They were then incubated in 5% sucrose in PBS for 1 h at 4° C. followed by a similar incubation in 10% sucrose in PBS and embedding in 7.5% gelatin with 20% sucrose. After snap freezing in 2-methyl butane, the blocks were stored at −80° C. Frozen sections, 8 μm thick, were cut in a cryostat, placed on gelatin-subbed slides and stored at −80° C.

For immunostaining, slides were allowed to stand at room temperature for 30 min and rinsed 3 times with warm PBS to remove gelatin. Non-specific binding sites were blocked by a 30 min treatment with 1% bovine serum albumin (BSA), containing 0.2% Tween-20 (Sigma) in PBS. Tissue was incubated with a polyclonal anti-PDGF-αR, C-20 (Santa Cruz Biotechnology, Santa Cruz, Calif.) at 0.5 μg/ml in blocking solution overnight at 4° C. After washing 3 times in PBS for 5 min, the sections were reacted with an anti-rabbit immunoglobulin antibody conjugated to Cy3 fluorochrome (Jackson ImmunoResearch Laboratories, West Grove, Pa.) for 1 h at room temperature. Nuclei were counterstained with YOPRO-1 iodide (Molecular Probes, Eugene, Oreg.).

Methacrylate Sections

Four rat utricles were cultured as above, two in control conditions and two in the neomycin treatment. After rinsing twice with PBS, they were fixed in 3% glutaraldehyde in phosphate buffer for 1 h, postfixed in 1% $OsO_2$ for 1 h, dehydrated in graded ethanols and embedded in methacrylate (Historesin, Leica). Sections, 3 μm thick, were mounted on slides and stained with toluidine blue for morphological analysis of tissue changes.

Figure 4:
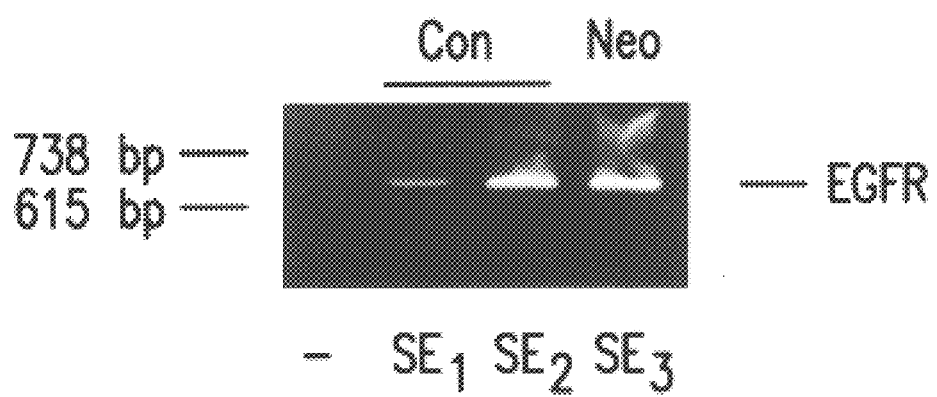
FIG. 4 shows amplified fragments for EGFR in control and neomycin-damaged sensory epithelia. Fragments of predicted size, 640 bp for EGFR, were visualized in a 3% metaphor gel with Sybr Green I dye. Numbers refer to base pairs of DNA standards: Con, control; Neo, neomycin damaged; SE, sensory epithelium; −, negative control, amplification of sequences in DEPC water.
Figure 5:
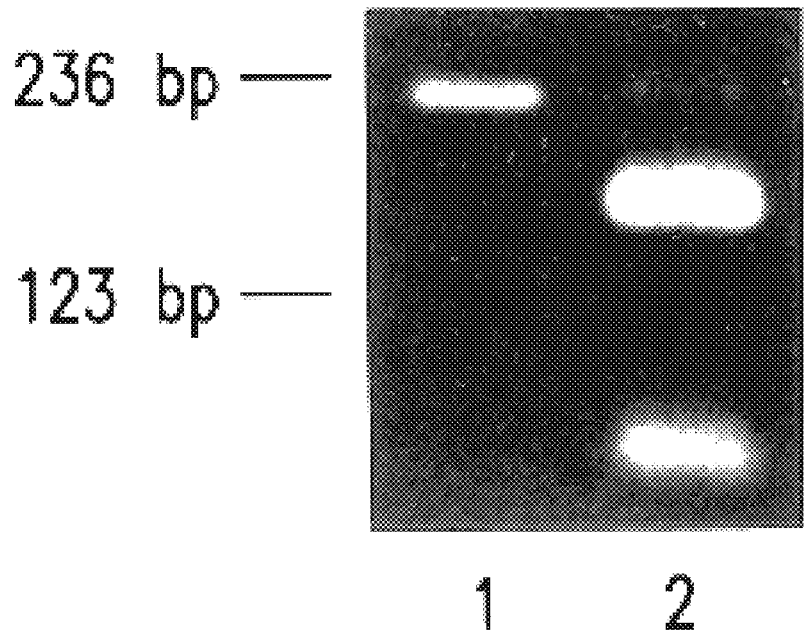
FIG. 5 shows the verification of the identity of the PDGF-αR fragment by digestion with Rsa I, an endonuclease that cuts DNA at the sequence 5'-GTAC-3'. The targeted PDGF-αR sequence contains a single Rsa I cleavage site. Digestion of the amplified fragment at the Rsa I site yielded two fragments of the sizes predicted from the sequence, one of 163 bp and another of 71 bp. Lane 1, undigested fragment (predicted size, 234 bp); Lane 2, digested fragment (predicted size, 163 and 71 bp).

Undamaged Sensory Epithelia from Utricles Express mRNA for Insulin R, IGF-IR, FGFR-I, EGFR, and PDGF-αR 4–8 individual sensory epithelia were assayed for each growth factor receptor message. Where the samples showed detectable levels of mRNA for β-actin, they also showed a fragment of the expected size the targeted growth factor receptor cDNA in every case except one. In 1 case, a sensory epithelium sample yielded a band for β-actin, but bands for Insulin R and FGFR-I were not detected. However, samples from 4 other sensory epithelia prepared according to the same protocol yielded the amplified band for Insulin R and 3 other sensory epithelia showed the amplified band for FGFR-I. The results were consistently like those illustrated in FIGS. 1–4. All amplified cDNA fragments of growth factor receptor messages were of the expected sizes. The identity of the PCR band for PDGF-αR was verified by digesting the cDNA product with the endonuclease Rsa I (FIG. 5). The digestion gave 2 fragments of 163 bp and 71 bp, the expected sizes based on the sequence specificity of the endonuclease. PCR products amplified for IGF-IR gave a pair of bands of similar size. Both bands appear to be fragments of IGF-IR cDNA because both were digested with endonuclease Msp I to give bands of expected sizes (data not shown). The smaller of the 2 bands was a doublet. A fragment of IGF-IR has been reported to amplify as a doublet, because a single base addition occurs inconsistently during the Taq polymerase reaction (Pedrini et al (1994) *Bio. Biophys. Res. Com.* 202:1038–1046.)

Hair Cell Loss was Produced by Culturing Sensory Epithelia with Neomycin

Figure 6A:
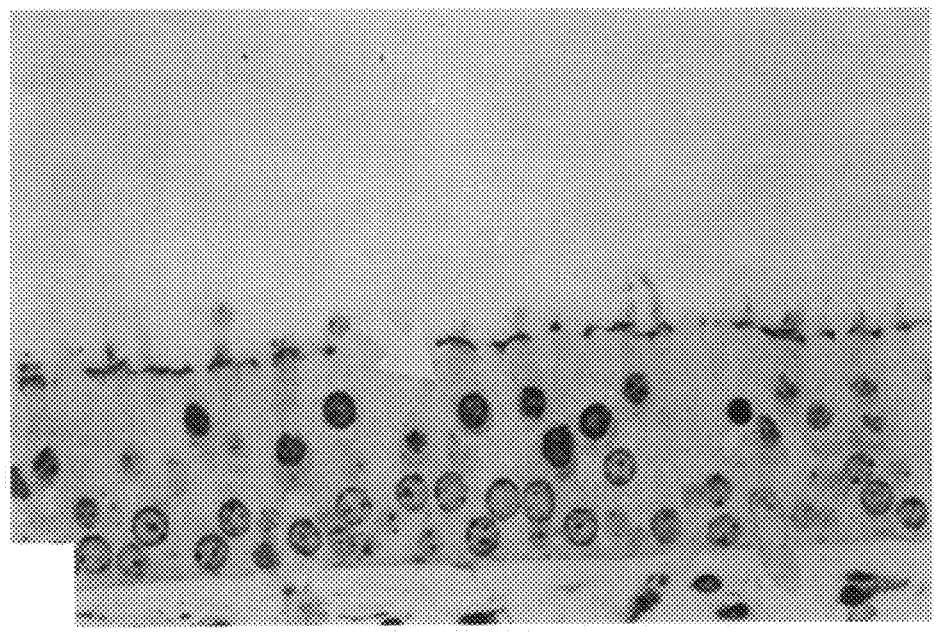
FIG. 6A shows an undamaged rat utricle which was cultured as a control.
Figure 6B:
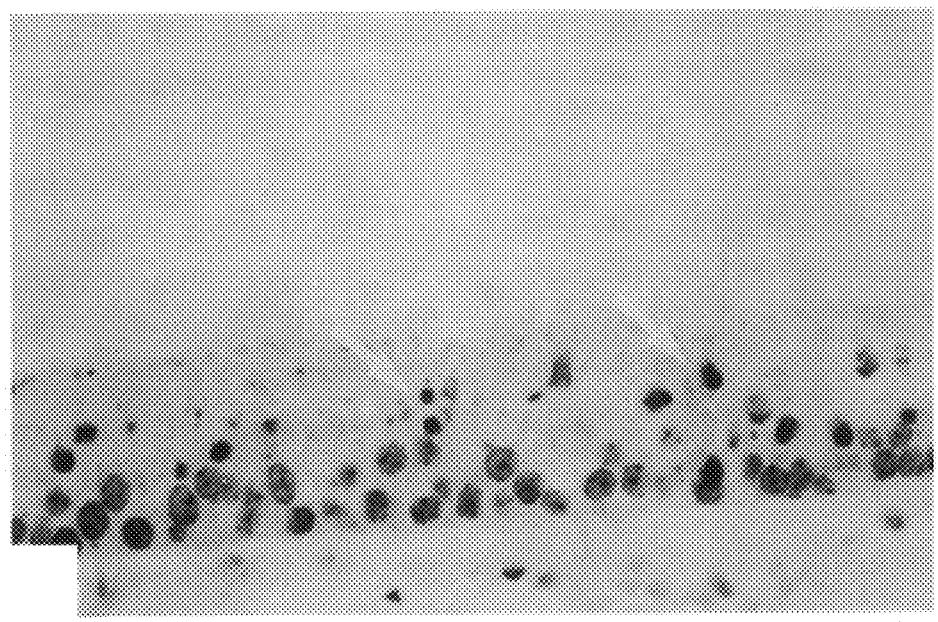
FIG. 6B shows a neomycin-damaged rat utricle. Arrows point to hair cell nuclei. Many of the remaining nuclei in the upper (hair cell) stratum of the neomycin-damaged sensory epithelium of the utricle are pycnotic.

At least 75% of the hair cells were lost from the utricles that were cultured in medium containing 10 mM neomycin for 24 h, followed by 24 h in medium without neomycin. Most remaining hair cells appeared abnormal with many containing pycnotic nuclei. The supporting cells appeared unchanged. In contrast, utricles cultured over the same period, but without neomycin, had normal appearing hair cells (FIG. 6).

Figure 1B:
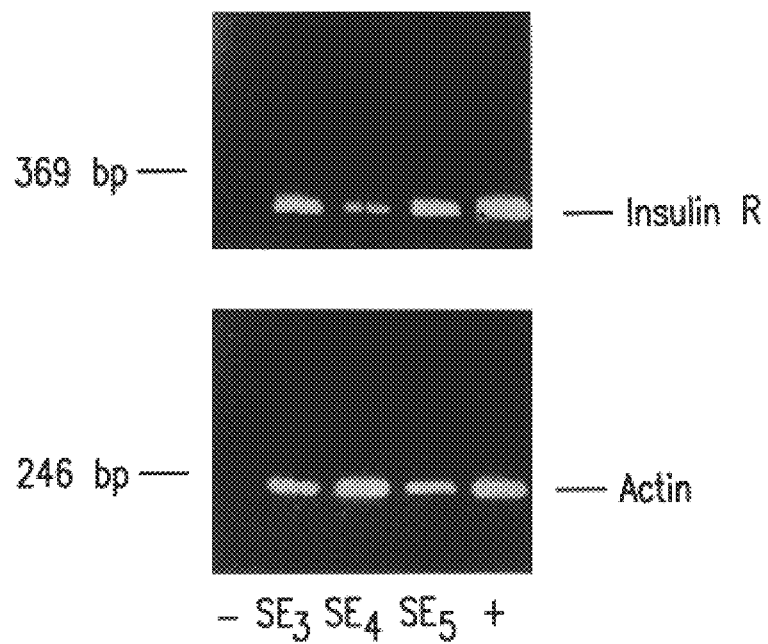
Figure 3:
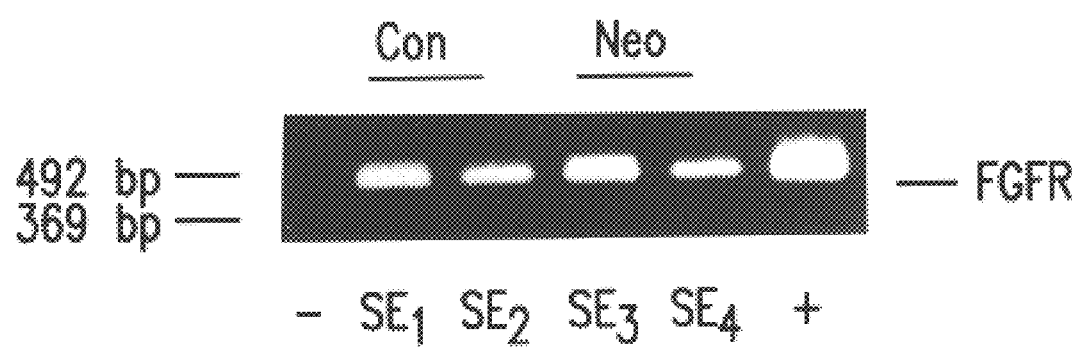
FIG. 3 shows amplified fragments for FGFR-I mRNA in control and neomycin-damaged sensory epithelia. Fragments of predicted size, 434 bp for FGFR-I, were visualized in a 3% metaphor gel with Sybr Green I dye. Numbers refer to base pairs of DNA standards: Con, control; Neo, neomycin damaged; SE, sensory epithelium; −, negative control, amplification of sequences in DEPC water; +, positive control, amplification of sequences in rat brain.

Neomycin-damaged Sensory Epithelia Showed Evidence of mRNA for Insulin R, FGFR-I, and EGFR FIG. 1 shows products from the RT-PCR assay for insulin R message in control and neomycin-damaged sensory epithelia as well as the products from the RT-PCR assay for β-actin message from the same samples of sensory epithelia. Three of 3 cases of control sensory epithelia showed the correct size PCR product for Insulin R message as did 4 of 4 cases for the neomycin-damaged sensory epithelia. In the case of FGFR-I, 4 of 4 control epithelia and 5 of 6 neomycin-damaged epithelia yielded bands of the appropriate size (FIG. 3). Assays for EGFR message yielded a single band of the appropriate size in 4 of 4 control and in 5 of 6 neomycin-damaged sensory epithelia (FIG. 4).

Levels of the PDGF-αR and IGF-IR Message Decreased After Neomycin Damage

Assays for the presence of PDGF-αR mRNA yielded bands in 8 of 8 cases for sensory epithelia cultured in the control medium, whereas the RT-PCR reactions for neomycin-damaged sensory epithelia showed no bands in 13 cases and weak bands in 2 of the 15 epithelia assayed with 35 cycles of PCR amplification (data not shown).

Figure 7:
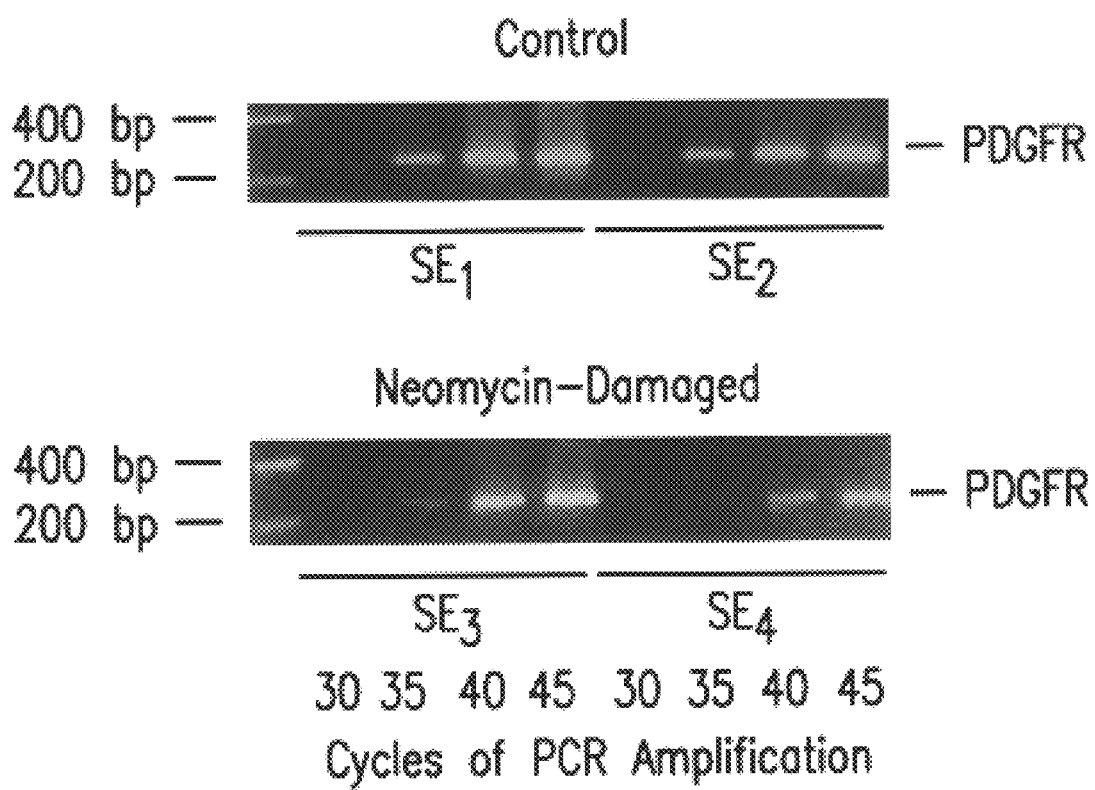
FIG. 7 shows semi-quantitative PCR which shows less mRNA from PDGF-αR in neomycin-damaged sensory epithelia than in control sensory epithelia. For comparison of the levels of messages in two different samples, it is necessary that the PCR reaction be in the exponential phase. At low numbers of cycles PCR amplification is exponential, but at high cycle numbers the efficiency decreases because reactants are depleted or the accumulated product interferes. Aliquots of the same sample were removed after different numbers of cycles of PCR and were visualized in a 3% metaphor gel with Sybr Green I dye. The exponential phase of the PCR reaction with the primers and conditions used here extends from at least 30 to 40 cycles. While the levels of two other messages measure in the same samples in their exponential phase appeared similar for neomycin-damaged and control epithelia, the levels of message for PDGF-αR showed a specific and reproducible decrease in neomycin-damaged sensory epithelia as compared with control epithelia.
Figure 8:
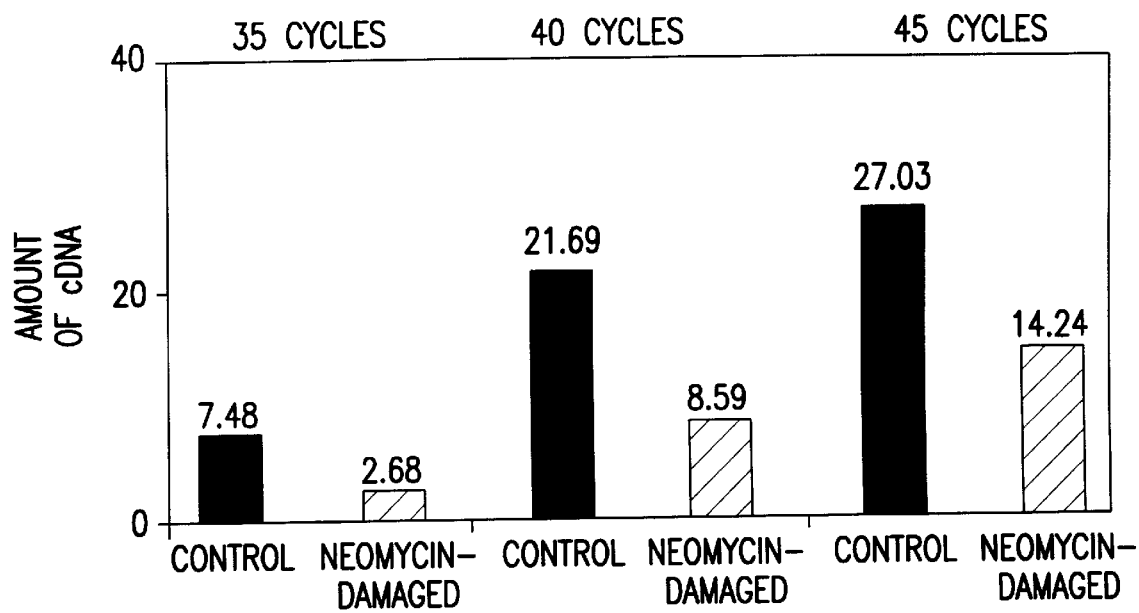
FIG. 8 shows measurements of the amounts of cDNA in the individual bands amplified from the sequence of PDGF-αR as illustrated in FIG. 7 showed that neomycin-damaged sensory epithelia yielded less cDNA than control sensory epithelia at 35 and 40 cycles of amplification. The intensity of each band was measured and compared to DNA standards which were run in the same gels. Numbers are nanograms of cDNA. Each band represents the average of 2 samples.

The exponential phase for the amplification of PDGF-αR was determined. The products amplified with primers for the PDGF-αR fragment did not yield detectable bands after 10, 15, 20, and 25 cycles of PCR, but a band of the expected size was detected after 30, 35, 40, and 45 cycles in samples from sensory epithelia cultured in control medium. The reactions using samples from sensory epithelia that had been damaged by neomycin yielded no detectable bands after 10, 15, 20, 25, and 30 cycles, but did yield bands after 35, 40, and 45 cycles (FIG. 7). Fluorometric measurements of the amount of cDNA in each of the bands provided quantitative evidence that neomycin-damaged sensory epithelia contained decreased levels of the PDGF-αR mRNA (FIG. 8). At 35 cycles the control sensory epithelia samples yielded on average 7.48 ng of amplified cDNA, whereas the neomycin-damaged sensory epithelia yielded 2.68 ng. At 40 cycles the control sensory epithelia yielded 21.69 ng of amplified cDNA, while the neomycin-damaged sensory epithelia yielded 8.59 ng. The exponential phase of PCR amplification for the PDGF-αR fragment amplified using the conditions and the primers chosen extends from at least 30–40 cycles, so these semi-quantitative results and the results from the earlier reactions that used 35 cycles of PCR both occurred in the appropriate range to reflect real differences in the levels of this mRNA.

As a control for potential variations in the amount of message extracted and as a control for variation in message stability, the PCR products for β-actin mRNA were assayed after 10, 15, 20, and 25 cycles in aliquots of the same samples used for the PDGF-αR mRNA. Neither control nor neomycin-damaged sensory epithelia yielded detectable bands for the β-actin fragment after 10 or 15 cycles of PCR. Both control and damaged samples yielded weak bands after 20 cycles and stronger bands after 25, 30, and 35 cycles (data not shown). Fluorometric measurements showed that the exponential phase for the β-actin amplification extended from at least 25 to 30 cycles.

Repetition of the semi-quantitative PCR experiment using two control and two neomycin-damaged sensory epithelia, and assaying for EGFR, as well as for PDGF-αR, after 30, 35, 40, and 45 cycles of PCR, and for β-actin after 20, 25, 30, and 35 cycles added further evidence of a specific neomycin-induced decrease in PDGF-αR and mRNA. The mRNA for EGFR was chosen for parallel control reactions in this experiment, because the EGFR cDNA fragment had yielded a weak band in the earlier assays that used 35 cycles of PCR. The weak appearance of the EGFR band in each of those experiments suggested that EGFR message might be present in a low number of copies in the samples of sensory epithelia, so that any potential variation in the efficiency of RNA extraction or in the stability of RNA, that could have confounded the PDGF-αR results, might be expected to appear in the semi-quantitative PCR of the EGFR fragment. As in the other semi-quantitative assays, the exponential phases of PCR amplification for PDGF-αR and EGFR fragments were found to extend from at least 30 to 40 cycles. The exponential range for the β-actin fragment extended from at least 20 to 30 cycles. The results again showed clearly detectable decreases in the mRNA for PDGF-αR in the neomycin-damaged sensory epithelia, whereas the message for EGFR, another growth factor receptor, and the message for β-actin, a cytoskeletal protein, did not show detectable decreases after the neomycin damage.

Figure 2:
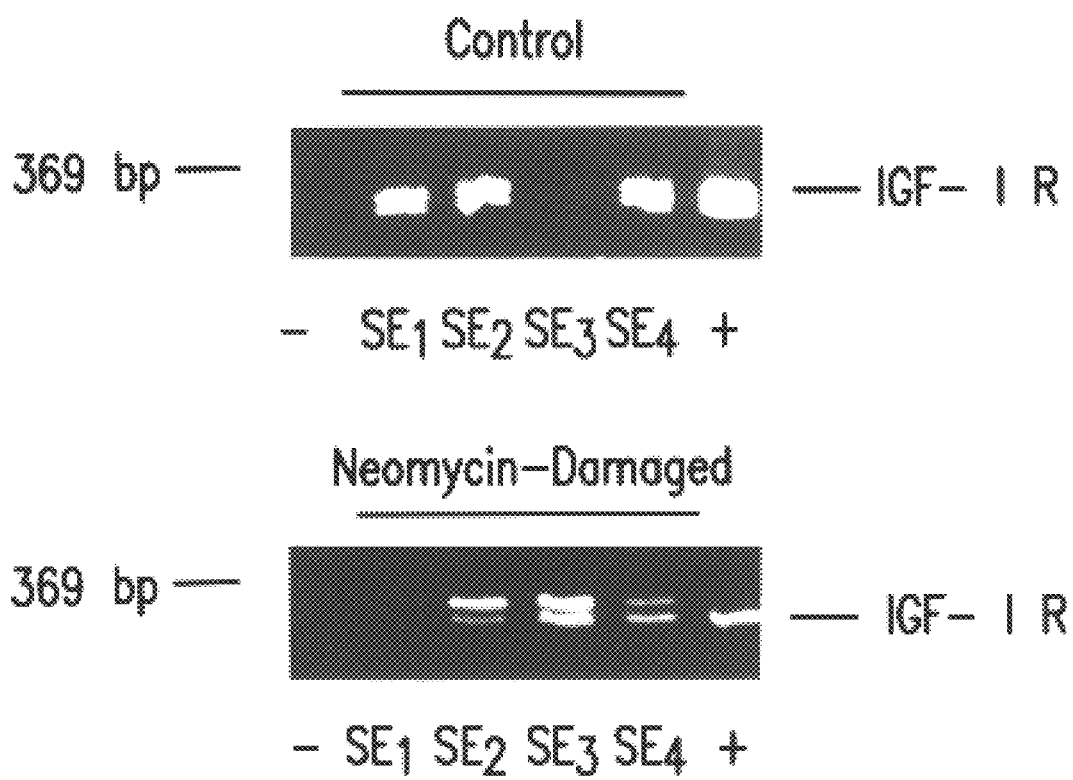
FIG. 2 shows amplified fragments for IGF-IR mRNA in control and neomycin-damaged sensory epithelia from rat utricles. Fragments of predicted size, 359 bp for IGF-IR, were visualized in a 3% metaphor gel with Sybr Green I dye. Both bands of the doublet appear to be amplified fragments of IGF-IR. The upper band is likely to be the result of extra base additions which have been reported to occur inconsistently during the Taq polymerase reaction (Pedrini et al, 1994). Numbers refer to base pairs of DNA standards: SE, sensory epithelium; −, negative control, amplification of sequences in DEPC water; +, positive control, amplification of sequences in rat brain.

Five of 5 control sensory epithelia showed the presence of mRNA for IGF-IR. The PCR products amplified for IGF-IR from cultured epithelia gave 2 bands, as had the in vivo epithelia. The sample from one of the control sensory epithelia yielded faint bands for IGF-IR that did not reproduce in the photograph (FIG. 2). Only 7 of 13 neomycin-damaged sensory epithelia gave evidence of IGF-IR message after 35 cycles of PCR. Therefore, this message was investigated by semi-quantitative PCR. The exponential range of PCR amplification extended from 30 to 40 cycles for the message. Using 2 in vitro control sensory epithelia and 2 neomycin-damaged sensory epithelia, 35 cycles of PCR yielded on average 13.9 ng of amplified cDNA for the controls, whereas the neomycin-damaged epithelia yielded no detectable cDNA. At 40 cycles, the controls yielded 113.5 ng of amplified cDNA, while the neomycin-damaged sensory epithelia yielded 27.4 ng.

Localization of the PDGF-αR to the Hair Cells

Figure 9A:
FIG. 9A shows localization of PDGF-αR to the hair cells of an undamaged rat utricle by fluorescent antibody staining. There is intense fluorescence of the supranuclear regions and the necks of type I hair cells (arrows) and the relative absence of labeling in the supporting cells.
Figure 9B:
FIG. 9B shows a view of the same section photographed with different optics to show the cell nuclei counterstained with YOPRO-1 iodide. The hair cell nuclei form an incomplete row in the apical half of the epithelium (the upper half in this micrograph). The nuclei of supporting cells form a nearly complete row at the base of the epithelium just above the connective tissue.

FIG. 9A shows a section of a control utricle that was incubated with an antibody to PDGF-αR. A fluorescently tagged secondary antibody was used to visualize the location of the primary antibody bound to PDGF-αR. Staining appeared in the hair cells, and most intensely in the supranuclear regions of type I hair cells. Supporting cells appeared unstained or much less stained. FIG. 9B shows the cell nuclei in the same section stained with YOPRO-1 iodide.

To understand the mechanisms by which hair cells are produced, caused to differentiate, and maintained throughout life, the elements of intercellular signaling cascades that control cell proliferation, cell differentiation, and cell survival in normal and traumatized otic sensory epithelia must be identified. As one approach to this problem, RT-PCR was used to determine whether mRNAs for certain growth factor receptors are detectable in samples of sensory epithelia from the utricles of rats. Samples from control rats yielded cDNA fragments of predicted size for mRNAs of Insulin R, IGF-IR, FGFR-1, EGFR, and PDGF-αR. Sensory epithelia that were damaged by neomycin in organ culture did not show noticeable differences in the levels of PCR products for the receptor mRNAs indicated above, with two exceptions. The exceptions were the message for PDGF-αR, which consistently gave lower levels of product in samples from neomycin-damaged epithelia as compared with the levels from in vitro and in vivo controls, and the message for IGF-IR, which gave lower levels of product in several neomycin-damaged epithelia.

RT-PCR is a rapid and sensitive method for the detection of mRNAs that may be labile and present in a low number of copies (Rappolee et al (1989) *J. Cell Biochem.* 39:1–11; Watson et al (1992) *Mol. Reprod. Dev.* 31:867–95.) It is possible to obtain false-positive results with this technique, because it is so sensitive, and therefore a number of precautions were taken against potential sources of false-positive findings. Each sensory epithelium sample was carefully separated from all underlying connective tissue and from surrounding epithelia, to ensure that the subsequent RT-PCR reactions would not amplify messages from other tissues. Several forms of controls were included in each PCR experiment to ensure contaminating genomic DNA or cDNA was had not been amplified. The sensory epithelia were also examined for the presence of β-actin message. The presence of this message is often used as a control to indicate the amount and integrity of mRNA in such preparations and as an internal control in quantitative PCR (Kinoshita et al., 1992). Actin is abundant in the hair cells and the supporting cells of the sensory epithelium of the utricle. The presence of β-actin mRNA in our samples provided an internal control to indicate that mRNA had been extracted successfully from each sensory epithelium brain tissue from the rat was used as a positive control sample and yielded amplified cDNA fragments of the expected size for each of the specific primer pairs used.

Since the 5 growth factor receptor mRNAs were present in the differentiated sensory epithelia of the rat utricle, there is a high likelihood that receptor proteins are being synthesized under the control of those mRNAs. The presence of growth factor receptor mRNA in the sensory epithelia of the utricle suggests that these 5 receptors are present on the surfaces of the supporting cells and/or the hair cells. The receptors should be able to bind the proper growth factors and trigger intracellular signal cascades thereby regulating growth, differentiation, or survival.

No difference was detectable in the occurrence of growth factor receptor messages between control sensory epithelia that were harvested from rats in vivo and those that were maintained in control culture medium for 48 h. The presence of serum did not appear to induce detectable changes in mRNA for growth factor receptors as determined here. Three of the same growth factor receptor mRNAs that were present in undamaged sensory epithelia, were also present in damaged epithelia, but there appeared to be less mRNA for PDGF-αR and IGF-IR in the neomycin-damaged tissue. It should be noted, however, that small changes in mRNA levels might not be detectable by the non-quantitative methods used to assay for Insulin R, FGFR-1, and EGFR.

In order to compare the levels of a message, it is necessary to be sure that the two enzyme steps in the RT-PCR reaction: the synthesis of cDNA from mRNA and the amplification of cDNA by PCR occur in such a manner that the product is representative of the amount of starting mRNA (Siebert (1993) In: Y. Munch, K. Mayo and A. Miller (Eds), Quantitative RT-PCR: *Methods and Applications,* Clontech, Palo Alto, Calif.) At low numbers of cycles PCR amplification is exponential, but at high cycle numbers the efficiency of amplification decreases because products accumulate or reactants become depleted. In order to determine the range of PCR cycles that spanned the exponential phase of amplification for PDGF-αR, EGFR, and β-actin cDNAs, aliquots of PCR products were removed after different numbers of cycles of PCR. The exponential phase was 30 to 40 cycles for the PDGF-αR and the EGFR cDNA fragments, and 20 to 30 cycles for the β-actin fragment.

Semi-quantitative assays produced data in that range of exponential amplification. Those data indicated that the level of mRNA for PDGF-αR was lower in neomycin-damaged sensory epithelia as compared to controls. To be certain that it was not differences in mRNA levels being detected because the samples contained fewer cells and less total RNA, or because the efficiency of RNA extraction was somehow systematically lower for the neomycin-damaged epithelia. To address those possibilities, we assayed two other messages that are expressed in the tissue. We examined the levels of β-actin mRNA and the levels of another receptor mRNA, EGFR. The levels of both messages appeared to be unchanged in the same samples where the levels of PDGF-αR mRNA showed clear decreases (4 samples). These results suggest that the decrease in PDGF-αR mRNA that resulted from neomycin treatment was specific to that message and was not the result of decreased total mRNA extraction.

From in vitro studies and histology, it is known that many hair cells were killed by the neomycin treatment, whereas the supporting cells appeared unharmed. As these experiments proceeded the hypothesis developed that PDGF-αR is expressed at higher levels in hair cells than in supporting cells. Consequently, the loss of hair cells caused by the neomycin treatment might have resulted in the measured drop in the level of mRNA for PDGF-αR. Subsequent application of immunohistochemistry with an antibody against PDGF-αR supported this idea, revealing much stronger staining in hair cells than in supporting cells (FIG. 9).

PDGF is a dimeric protein composed of two similar chains linked by disulfide bonds. It exists in three forms, the homodimers AA, and BB, and the heterodimer AB. There are two receptors for the isoforms of PDGF, α and β receptors, which are membrane proteins with an extracellular domain that binds the growth factor and an intracellular tyrosine kinase domain. Ligand binding causes PDGF receptors to dimerize in the membrane resulting in kinase activation. PDGF-αR can bind both A and B chains of PDGF, whereas PDGF-βR binds only the B chain. PDGF is a mitogen for connective tissue, glia, and smooth muscle cells. In some fibroblasts, PDGF can stimulate synthesis of collagens and other matrix proteins. PDGF also can have neurotrophic effects (Raines et al (1991) Platelet-derived growth factor. In: M. B. Spron and A. B. Roberts (Eds.) *Peptide Growth Factors and Their Receptors I. Springer, New York, N.Y.;* Smits et al (1991) *Proc. Natl. Acad. Sci. USA* 88: 8159–8163.) Mature hair cells have not been reported to undergo mitosis, so it seems likely that PDGF binding to hair cells, if active, would function in another role.

A convincing argument has been made that all mammalian cells with the exception of blastomers of the early embryo, require extracellular signals form other cells in order to survive (Raff et al (1993) *Science* 262:695–700.) Such survival factors bind to cell surface receptors. Cells that do not receive the required amount of survival factors, cells that have lost the receptors for available survival factors, and cells in which the intracellular survival signaling cascades have been blocked all die by programmed cell death (apoptosis). Hair cells in vestibular and auditory sensory epithelia which have been damaged by aminoglycoside antibiotics or by acoustic overstimulation can also die by apoptosis (Jorgenson (1991) Regeneration of lateral line and inner ear vestibular cells. In: *Regeneration of Vertebrate Sensory Receptor Cells.* Wiley. Chichester (Ciba Found. Symp. 160) pp. 151–170; Li et al (1995) *J. Comp. Neurol.* 355:405–417; Kil et al (1995) *Assoc. Res. Otolaryng. Abstr.* 18:82; Mason et al (1995) *Soc. Neurosci. Abstr.* 20:396.)

An elegant series of experiments on the growth and survival requirements of glial cells in the optic nerve have demonstrated that PDGF can promote the survival of immature oligodendrocytes by preventing activation of the apoptotic suicide program which would kill cells in the absence of such a factor (Barres and Raff (1994) *Neuron* 12:935–942.) By analogy it seems reasonable to hypothesize that the indications of mRNA and protein for the PDGF-αR observed in hair cells may relate to a survival control function for extracellular PDGF in this cell type. In the future it will be important to test that hypothesis experimentally.

Evidence from PCR at 35 cycles and preliminary evidence from semi-quantitative PCR have suggested that mRNA for IGF-IR also decreases in utricular sensory epithelia along with decreases in the number of hair cells that survive after neomycin treatment. Like PDGF, IGF-1 is a known survival factor for immature oligodendrocytes, but it does not induce proliferation of those cells or their precursors. IGF-1 also has survival promoting effects on cells from the kidney and motorneurons (Raff et al (1993) *Science* 262:695–700.) In view of the survival promoting effects of IGF-1 in those cell types and evidence for decreased levels of IGF-IR MRNA occurring along with neomycin-induced loss of hair cells, IGF-I may have a role in the normal survival of hair cells in the mammalian ear. Hair cell loss in response to a variety of insults can occur via an apoptotic mechanism which depends on the activation of a suicide program within the cell. As the results of this investigation have shown, hair cells express receptors specific for extracellular signaling factors that are known to prevent the execution of the apoptotic suicide program in other cell types. The results confirm that pharmacological methods, including the administration of growth factors can protect ears from the loss of hair cells caused by traumatic insults. Age-related loss of hair cells can also be prevented using such growth factor therapeutics which contribute to the replacement of decreased levels of normal survival signals or provide augmentation of the resistance of hair cells to insults that might otherwise trigger the activation of an apoptotic suicide program.

Example 2

White leghorn chicks (*Gallus domesticus*, 8 to 16 days post-hatch) were euthanized via $CO_2$ asphyxiation, decapitated, demandibulized, and scalped. The heads were soaked in chilled 95% EtOH until dissection (5–60 minutes), in order to kill surface pathogens. The remaining dissection was carried out under microscopic guidance in a laminar flow sterile tissue aculture hood. Saccules, along with the surrounding temporal bone, were removed bilaterally from each head and placed in a Sylgard dish containing sterile Medium-199 with Hanks salts, 0.69 mM L-glutamine, and 25 mM HEPES (Gibco BRL Life Technologies). The otoconia were removed using fine forceps and the saccules were released from bone, and placed in culture wells (NUNC 177402) in 200 µl of medium (as described below).

The basal culture medium consisted of 200 µl of Medium-199 with Earles Salts, 0.69 mM L-glutamine, 0.26 mM sodium bicarbonate, and 25 mM HEPES, supplemented with 10% FBS (Gibco BRL Life Technologies). Ninety saccules were placed in culture as described. Forty-six saccules were cultured in the basal medium alone, while 44 saccules were cultured in medium that also contained IGF-1 (100 ng/ml, Amersham Life Science). The specimens were incubated at 37° C. in a humidified chamber with an atmosphere of 5% $CO_2$.

After 24 hours, approximately half of the saccules in each group (21 saccules in IGF-1-containing medium, 20 saccules in basal medium alone) received 2 µl of 100 mM neomycin sulfate (dissolved in basal medium). Thus, the medium in those cultures now contained 1 mM neomycin. All cultures were then incubated (as described above) for an additional 24 hours. At this time, the saccules were removed from the incubator, and fixed in 4% paraformaldehyde (in 0.1 M phosphate buffer) for 1 hour at room temperature. Tissues were then rinsed in 0.1M PBS and placed in 90% MeOH/0.5% $H_2O_2$ for 15 minutes to reduce endogenous peroxidase activity. Non-specific antibody binding was blocked by incubation in 5% non-fat dry milk/2% BSA solution for 20 minutes. Following rinsing in 0.1M PBS, apoptotic nuclei were visualized by the addition of digoxigenin-dUTP to the free 3'-OH ends of DNA via terminal deoxynucleotidyl transferase (tdt) catalysis using the protocol established in the ApopTag In Situ Apoptosis Detection Kit (Cat. no. S7100-KIT, Oncor, Inc.). Tissues were placed in equilibration buffer for 5 minutes, and then transferred to reaction buffer containing digoxigenin-dUTP and tdt, and incubated in a humidified chamber at 37° C. for 1 hour. Digoxigenin-dUTP incorporation was stopped by removing the reaction buffer and by further incubation of the epithelia in stop/wash buffer at 37° C. for 30 minutes, with agitation every 10 minutes. Tissues were rinsed in 0.1M PBS and exposed to an anti-digoxigenin peroxidase-conjugated antibody (1:50 dilution) for 30 minutes at room temperature. Specimens were then rinsed in 0.1 M PBS and stained with a solution of $DAB/Ni/H_2O_2$ (Vector, Inc.) for 6 minutes. Tissues were rinsed in 0.1 M PBS and coverslipped with Gel mount (Biomeda, Inc.). Individual slides were labeled as to treatment, but this label was obscured during quantification. Cell counts were performed under 'blind' conditions, such that the person who performed the counts did not know the culture conditions of any individual specimen.

The number of apoptotic cells in each saccule were counted using a Leitz Dialux 20 microscope, using differential interference contrast (DIC) optics and a 40× objective lens. Quantification was achieved in the following manner: a 25-square grid in the eyepiece was positioned over one quadrant of the saccule interior enough to avoid the edge and any folded tissue. Labeled apoptotic cells were then counted in 13 preselected squares of the grid. The grid was moved to each quadrant and the count repeated and recorded. Only stained cells in the sensory epithelium of the saccule were counted; labeled cells in the deep connective and neural tissue were not quantified. In order to maintain consistency and reliability between cell counts, criteria were established to discard saccules in cases of evident sensory epithelial traumatic damage Quantitative data on labeled apoptotic cells was classified into groups: (A) neomycin alone, (B) IGF-1 alone, (C) neomycin and IGF-1, and (D) controls. The quadrant counts (n=360) were compiled and analyzed by Scheffe's test for general linear models.

Apoptotic cells in the sensory epithelia 360 saccule quadrants were counted under microscopic visualization. The numbers of sampled quadrants in each group were: (A) 80 in saccules treated with neomycin alone, (B) 92 in saccules treated with IGF-1 alone, (C) 84 in saccules treated with neomycin and IGF-1, and (D) 104 quadrants in untreated (control) saccules. The mean numbers of apoptotic cells in each group were (mean ±standard deviation):

| | |
|---|---|
| Neomycin alone: | 59.0 ± 19.2 |
| IGF-1 alone: | 14.3 ± 5.8 |
| Neomycin + IGF-1: | 36.7 ± 15.6 |
| Control: | 22.6 ± 11.3 |

Figure 10:
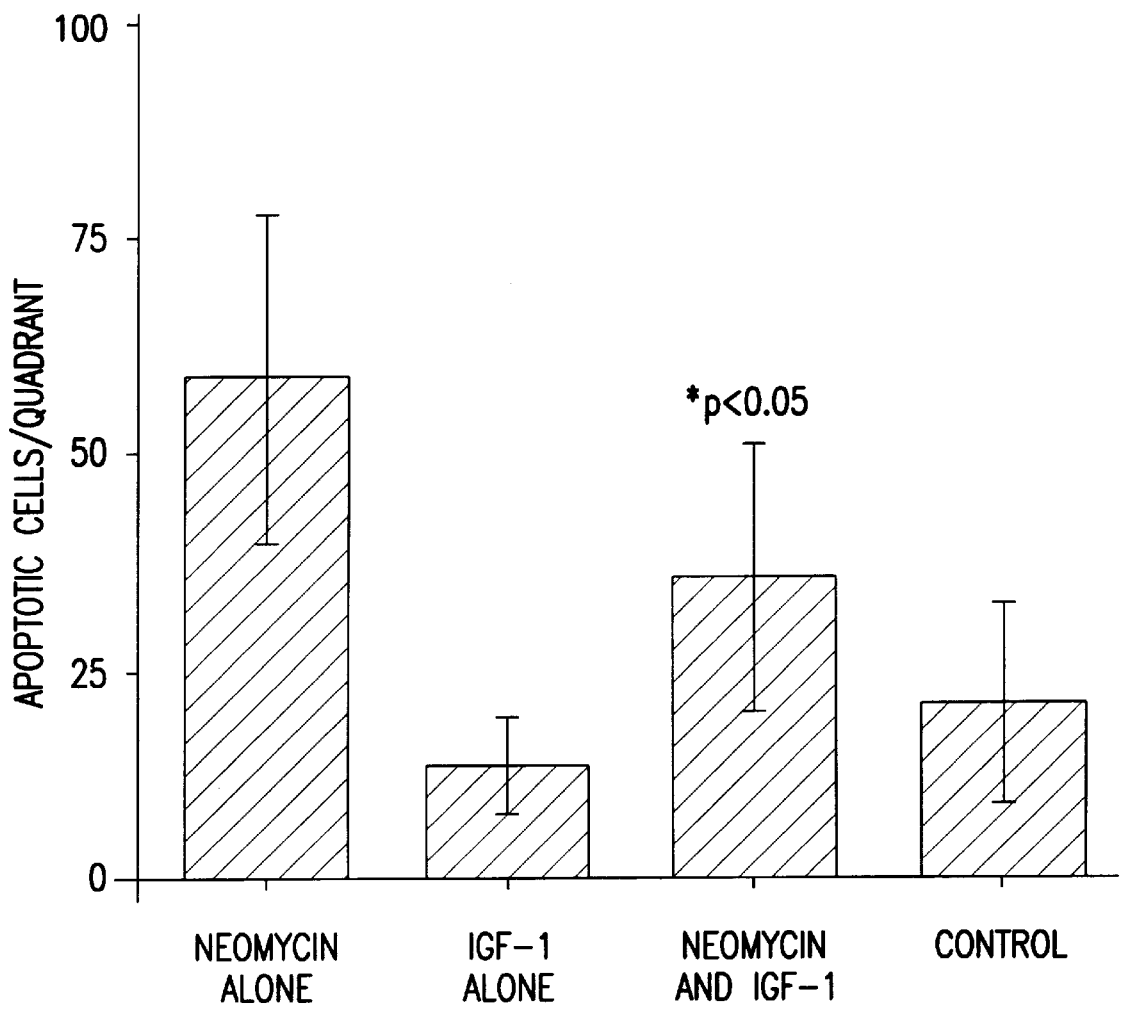
FIG. 10 shows the effect of IGF-1 Treatment on neomycin-induced apoptosis in the inner ear.

Statistical analysis (Scheffe's test for general linear models) demonstrated that the number of labeled apoptotic cells in the saccules that were treated with neomycin and IGF-1 was significantly less that the number of apoptotic cells that was present in saccules that were treated with neomycin alone (p<0.05). In the cultured saccules, IGF-1 treatment reduced aminoglycoside-induced apoptosis by 38% (see FIG. 10). This result demonstrates that IGF-1 has a protective effect in saccular hair cells and supporting cells against apoptosis-effecting neomycin.

Thus, growth factors, and in particular IGF-1 and PDGF protect the inner ear from loss of sensory hair cells caused by drug toxicity, trauma, and processes underlying age-related loss of hearing and balance sensitivity.

Having now fully described the invention, it will be apparent to one of ordinary skill in the art that many changes and modifications can be made thereto without departing from the spirit or scope of the invention as set forth herein.

What is claimed as new and is desired to be secured by Letters Patent of the United States is:

1. A method for preventing loss of sensory hair cells in an inner ear of a vertebrate in need of such treatment, comprising administering a therapeutically effective amount of at least one growth factor selected from the group consisting of an insulin-like growth factor and platelet-derived growth factor to said vertebrate, wherein said at least one growth factor binds to a receptor specific for said growth factor on said hair cells, and wherein a detectable level of said receptor decreases upon exposure of said hair cells to an ototoxic drug.

2. The method of claim 1, wherein said growth factor is an insulin-like growth factor.

3. The method of claim 2, wherein said insulin-like growth factor is IGF-1.

4. The method of claim 1, wherein said growth factor is platelet-derived growth factor.

5. The method of claim 1, wherein the method protects against damage to said sensory hair cells caused by said ototoxic drug.

6. The method of claim 5, wherein said ototoxic drug is an aminoglycoside antibiotic.

7. The method of claim 1, wherein said vertebrate is a mammal.

8. The method of claim 1, wherein the method protects against damage to said sensory hair cells caused by aging.

* * * * *